United States Patent [19]
Planker et al.

[11] Patent Number: 4,952,697
[45] Date of Patent: Aug. 28, 1990

[54] PROCESS FOR THE PREPARATION OF 2-NITRO-3-AMINOPYRIDINE, AND THE INTERMEDIATES WHICH ARE FORMED IN THE REACTION

[75] Inventors: Siegfried Planker, Königstein/Taunus; Klaus Warning, Eppstein/Taunus; Günter H. Herbst, deceased, late of Kelkheim (Taunus), Ingrid L. M. Herbst née Badewitz, heir; Ulrike M. Herbst, Kelkheim (Taunus); Bettina S. Herbst, Kelkheim (Taunus); Georg Schaeffer, Hofheim am Taunus, all of Fed. Rep. of Germany

[73] Assignee: Hoechst Aktiengesellschaft, Frankfurt am Main, Fed. Rep. of Germany

[21] Appl. No.: 238,968

[22] Filed: Aug. 25, 1988

Related U.S. Application Data

[63] Continuation-in-part of Ser. No. 932,170, Nov. 18, 1986, abandoned, which is a continuation-in-part of Ser. No. 818,125, Jan. 10, 1986, abandoned.

[30] Foreign Application Priority Data

Jan. 12, 1985 [DE] Fed. Rep. of Germany ....... 3500910

[51] Int. Cl.$^5$ ............................................. C07D 401/12
[52] U.S. Cl. ..................................... 546/265; 546/307
[58] Field of Search ................................. 546/265, 307

[56] References Cited
PUBLICATIONS

Hackley et al., Chemical Abstracts, vol. 50(7), pp.–49-47–4948, Apr. 10, 1956.
Clark-Lewis, J. W., and Thompson, M. J., "Methylation of 3-Aminopyridines and Preparation of 2-Amino-3 Methylaminopyridine and 2: 3-Diaminopyridine", *J. Chem. Soc.*, 442–446 (London 1957).

*Primary Examiner*—Alan L. Rotman
*Attorney, Agent, or Firm*—Curtis, Morris & Safford

[57] ABSTRACT

2-Nitro-3-aminopyridine is prepared by
(a) reacting 3-aminopyridine with phosgen $COCl_2$ or urea $H_2NCONH_2$ to give N,N'-di-(3-pyridyl)-urea,
(b) nitrating and N,N'-di-(3-pyridyl)-urea with nitric acid or with a mixture of nitric acid and sulfuric acid to give N,N'-di-(2-nitor-3-pyridyl)-urea, and
(c) hydrolyzing said N,N'-di-(2-nitro-3-pyridyl)-urea to give 2-nitro-3-amino-pyridine.

N,N'-di-(3-pyridyl)-urea and N,N'-di-(2-nitro-3-pyridyl)-urea, which are formed in the course of the reaction as intermediates are new compounds.

The end product of the process, 2-nitro-3-aminonpyridine, is an intermediate in various specialized fields.

8 Claims, No Drawings

PROCESS FOR THE PREPARATION OF 2-NITRO-3-AMINOPYRIDINE, AND THE INTERMEDIATES WHICH ARE FORMED IN THE REACTION

This application is a continuation-in-part of application Ser. No. 07/932,170, filed Nov. 18, 1986 abandoned which is a continuation-in-part of application Ser. No. 06/818,125, filed Jan. 10, 1986 abandoned.

2-Nitro-3-aminopyridine is the compound of the formula

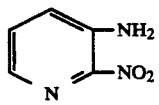

It is principally a valuable intermediate in various specialized fields, such as the pharmaceutical, dyestuff and plant protection sector. Thus, for example, 2-nitro-3-aminoalkylaminopyridines which can be employed in the pharmaceutical sector for combating amebic infections (German Patent No. A-2,334,401) are obtained by reacting 2-nitro-3-aminopyridine with aminoalkyl halides.

2-Nitro-3-aminopyridine is not obtainable, or, if so, only in traces, by the direct nitration of 3-aminopyridine, which is readily accessible—for example by Hofmann's degradation of nicotinamide—and is also commercially available; this is scarcely surprising because of the known sensitivity of the (unprotected) amino group toward nitrating agents—which have usually also an oxidizing action.

If, therefore—following the article by J. W. Clark-Lewis and M. J. Thompson in J. Chem. Soc. (London) 1957, pages 442 to 446, in particular pages 445/446 -3-ethoxycarbonyl-aminopyridine is used as the starting material, the nitration is stated to take place in a yield up to 65%, if, and only if, the nitration is carried out in small batches, since the nitro compound formed is not stable under the conditions applied and tends to explosion in larger batches. The 2-nitro-3-ethoxycarbonylaminopyridine formed in the reaction then affords the desired 2-nitro-3-aminopyridine by alkaline hydrolysis; the yield quoted for the hydrolysis stage is 86%. Relative to the 3-ethoxycarbonylaminopyridine, the yield is thus about 56%.

In outline, the equations on which this reaction is based are as follows:

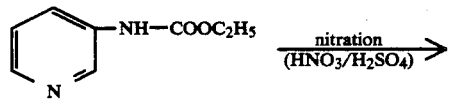

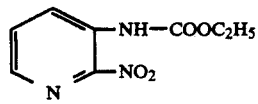

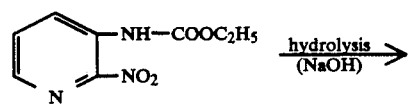

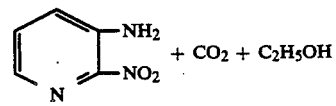

Following the literature reference mentioned above, the starting material for this reaction (3-ethoxycarbonylaminopyridine) is obtained, starting from nicotinic acid, by the following reaction sequence:

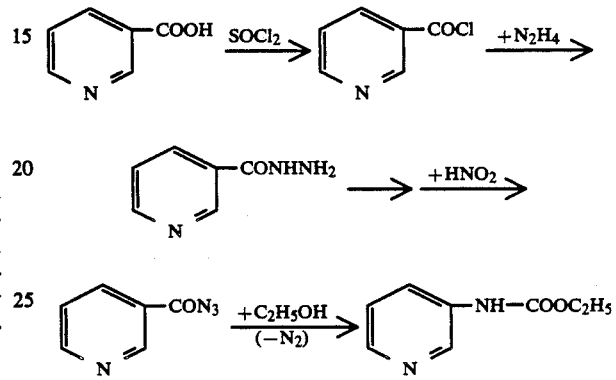

The introduction of other protective groups for the amino group has—as our own experiments have shown—proved unsuitable, since in some cases decomposition takes place in the course of the nitration (as in the reaction according to J. W. Clark-Lewis and M. J. Thompson, loc. cit.); in some cases the nitro group enters a position in the pyridine ring other than the desired 2-position. The protective groups and classes of protective groups tested were as follows:

—COCH$_3$,
—COC$_6$H$_5$,
—CO—C$_6$H$_4$—NO$_2$,
—COOCH$_3$,
—COOC$_6$H$_5$,
—CONR$^1{}_2$ (R$^1$ = C$_1$-C$_4$-alkyl),
—CONHR$^1$ (R$^1$ = C$_1$-C$_4$-alkyl),
—SO$_2$R$^2$ (R$^2$ = C$_1$-C$_4$-alkyl , or optionally substituted phenyl).

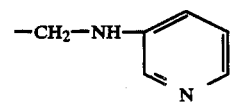

In the purely aromatic (not heterocyclic) series, disclosure has also been made of the nitration of an aniline derivative (2-methoxyaniline) which has been converted into a urea derivative (bis-2-methoxyphenylurea) before the nitration in order to protect the amino group. In this case the nitration took place in the 4-position. The reaction is published in Chemical Abstracts, Volume 49 (1955), 5341i to 5342b; the publication represents the abstract of a paper by D. F. Kutepov and Z. G. Vukolova, Zh. Obsc. Khim. 24, 698–792 (1954).

In outline, the decisive reaction sequence here is as follows:

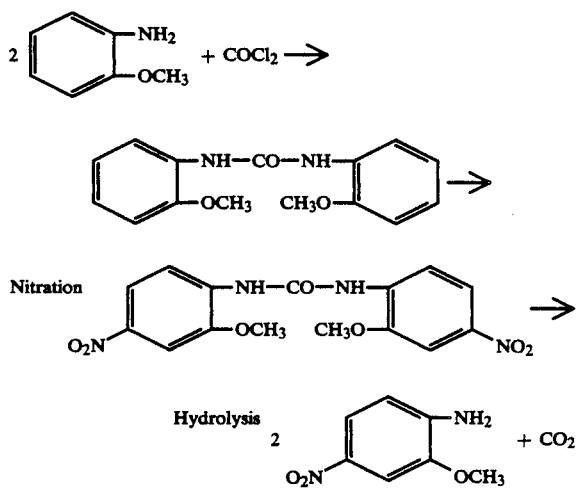

In the endeavour to provide an improved process for the preparation of 2-nitro-3-aminopyridine, it has now been found that this object is achieved by the nitration and hydrolytic cleavage of N,N'-di-(3-pyridyl)-urea.

The invention relates, therefore, to a process for the preparation of 2-nitro-3-aminopyridine by
(a) reacting 3-aminopyridine with phosgene $COCl_2$ or urea $H_2NCONH_2$ to give N,N'-di-(3-pyridyl)-urea,
(b) nitrating said N,N'-di(3-pyridyl)-urea with nitric acid or with a mixture of nitric acid and sulfuric acid to give N,N'-di-(2-nitro-3-pyridyl)-urea, and
(c) hydrolyzing said N,N'-di-(2-nitro-3-pyridyl)-urea to give 2-nitro-3-amino-pyridine.

The process is based on the following reaction equations:

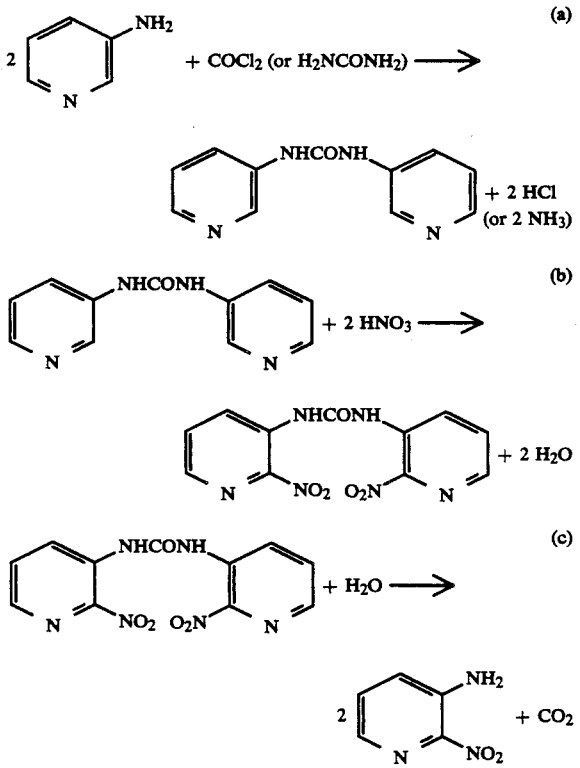

The reaction (a) of the process according to the invention is performed in a customary manner as for example, described for the reaction of 2-aminopyridine with phosgene or urea in Beilstein H 22, 330, with a nearly quantitative yield.

Reaction (b) of the process according to the invention—i.e. the nitration of the N,N'-di-(3-pyridyl)-urea—takes place safely, in a very readily controllable manner and extremely selectively only in the (desired) 2-position in the pyridine ring and in high yields (consistently over 90% of theory).

Reaction (c)—i.e. the hydrolysis of the N,N'-di-(2-nitro-3-pyridyl)-urea—also takes place in yields consistently over 90% of theory, so that the overall yield of the process is usually around or over 80% of theory, relative to the starting compound 3-aminopyridine.

In particular, the extremely selective and smooth nitration in general, and in particular in the 2-position, is very surprising, because as shown by our own tests mentioned earlier and described below, the nitration either leads to decomposition or proceeds in an undesired position, when the 3-aminopyridine is protected by protective groups other than the urea group applied according to the present invention.

The conversion of 3-aminopyridine into N,N'-di-(3-pyridyl)-urea is preferably performed analogous to the reaction of 2-aminopyridine with phosgene or urea as described in the before-mentioned Beilstein reference. For this purpose the 3-aminopyridine is heated with $COCl_2$ or $H_2NCONH_2$ in a molar ratio of about 2:1, whereby minor deviations form the stoichiometric proportions are possible without impairing the reaction. The reaction can also be performed in inert organic solvents such as chlorobenzene, dichlorobenzenes, toluene and/or chlorotoluenes, etc. In the event of the reaction with $COCl_2$, usual temperatures are between about 30° and 120° C., in the event of the reaction with $H_2NCONH_2$ between about 120° and 190° C. Both reactions can be carried out under atmospheric pressure as well as under superatmospheric pressure; sub-atmospheric pressure is less advantageous. Superatmospheric pressure is particularly advisable when an inert organic solvent is used, the boiling point of which is below the reaction temperature.

The nitration of the N,N'-di-(3-pyridyl)-urea is carried out in the manner customary for nitration reactions of this type by means of nitric acid, in the presence of sulfuric acid. For example, it is possible initially to take N,N'-di-(3-pyridyl)-urea in sulfuric acid or oleum and then to add nitric acid or a mixture of nitric and sulfuric acid (nitrating acid), or, for instance, also to introduce solid N,N'-di-(3-pyridyl)-urea into a previously taken mixture of nitric acid and sulfuric acid.

The reaction temperature is not particularly critical in this process, but the temperature should not substantially exceed about 90° C. for reasons of process safety and quality of the product. The reaction is preferably carried out at about 50°–70° C.

The components N,N'-di-(3-pyridyl)-urea and $HNO_3$ are preferably employed in a molar ratio of 0.5:about 1–2, in particular 0.5:about 1.2–1.4.

The N,N'-di-(2-nitro-3-pyridyl)-urea formed in the nitration can be isolated in a customary manner, for example by adding water to the reaction mixture when the reaction is complete and thus precipitating the desired product in a solid form, so that it can be obtained in a pure form by filtration or centrifuging.

N,N'-di-(2-nitro-3-pyridyl)-urea is a new compound.

In principle, the hydrolysis of the latter compound can be carried out in excess water; it is preferably, however, to add polar solvents, in particular alcohols. Acids or bases can be added to accelerate the reaction, as is known per se in the case of the hydrolysis of urea derivatives. In the present case, a preferred method of carrying out the hydrolysis is to effect it by means of inorganic bases (NaOH, KOH, NH$_3$ etc.) in an aqueous C$_1$–C$_4$-alcohol (methanol, ethanol, isopropanol etc.), because the CO$_2$ formed in the course of the hydrolysis is then immediately fixed as the carbonate or bicarbonate of the particular base.

For example, aqueous sodium hydroxide solution is metered into a suspension of N,N'-di-(2-nitro-3-pyridyl)-urea in a lower alcohol, such as methanol or ethanol, the urea derivative: NaOH molar ratio being preferably about 1:1–3, especially about 1:1.5–2. The 2-nitro-3-aminopyridine crystallizes out toward the end of the reaction, and can be isolated in a pure form.

The examples which follow are intended to illustrate the invention further. The examples of the invention (A) are followed by a number of comparison examples (B) which show that the nitration of 3-aminopyridine in which the amino group is substituted by other protective groups does not lead to the desired objective (nitration in the 2-position in good yields and in a controllable reaction).

(A) EXAMPLES OF THE INVENTION

EXAMPLE 1

(a) Reaction of 3-aminopyridine with urea:

To 1000 g of o-Cl-toluene (=solvent), which was placed in a 4 liter flask provided with stirrer, thermometer and reflux-condenser,
470 g=5 moles of 3-aminopyridine, and
150 g=2.5 moles of urea
were added.

For preventing the NH$_3$-formation from becoming too vehement, the reaction was carried out in several temperature-stages. First, the reaction mixture was heated for about 1 hour to 130° C.; the NH$_3$-formation, which began between 120°–130° C., became slower at the end of this heating period. Then, the temperature was elevated and kept for 1 hour at 140° C., and further elevated and again kept for 1 hour at 150° C. Thereafter at 150° C. about 20 liters of nitrogen (N$_2$) per hour were blown through the reaction mixture up to the crystallization of the di-(3-pyridyl)-urea, which had first been formed as an oily layer. For completing the reaction, the reaction mixture was heated with refluxing to about 160° C. for ca. 4–5 hours without N$_2$ passing through. The reaction mixture was then allowed to cool up to room temperature, at which temperature the di-(3-pyridyl)-urea that has precipitated was sucked off.

Thus, about 578 g of a violet-pink-coloured crystalline product being still moist with solvent was obtained. The product was dried at about 100° C. under reduced pressure.

The yield of the dried (raw) di-(3-pyridyl)-urea was ca. 519 g=97% of theory; m.p. 225°–227° C. (the purified product melted at ca. 228° C.).

(b) Nitration:

400 g of 10% strength oleum and 100 g (0.47 mol) of N,N'-di-(3-pyridyl)-urea were placed in a 1.5 liter stirred apparatus and 238 g of nitrating acid of the composition 32% of HNO$_3$ and 68% of H$_2$SO$_4$ were added in the course of 1.5 hours at a reaction temperature of 60° C. Stirring was then continued for 3 hours at this temperature, and the mixture was cooled to room temperature and diluted with 780 ml of water. The suspension was subsequently stirred at 20° C.; the reaction product was then filtered off with suction and washed until neutral.

Yield: 133 g of N,N'-di-(2-nitro-3-pyridyl)-urea=93% of theory, melting point: 230°–233° C. with decomposition. The NMR and IR spectra were in agreement with the structure mentioned.

(c) Hydrolysis:

Hydrolysis was carried out by placing 415 g of ethanol in a 1.5 liter stirred apparatus and introducing 133 g (0.44 mol) of N,N'-di-(2-nitropyridyl)-urea. The suspension was heated at 70° C. and 300 g of 10% strength sodium hydroxide solution were added. The 2-nitro-3-aminopyridine was partially precipitated during the reaction. In order to achieve complete precipitation of the reaction product, the mixture was diluted with approx. 500 ml of water after the completion of the reaction and cooled to 0° to +5° C., the suspension was filtered with suction and the reaction product was washed until neutral.

Yield: 109.6 g of 2-nitro-3-aminopyridine=90.4% of theory, relative to N,N'-di-(2-nitro-3-pyridyl)-urea. Melting point: 199°–200° C.

EXAMPLE 2

400 g of 10% strength oleum and 238 g of nitrating acid of the composition 32% of HNO$_3$ and 68% of H$_2$SO$_4$ were placed in a 1.5 liter stirred apparatus, and 100 g of N,N'di-(3-pyridyl)-urea (prepared as in Example 1a) were introduced in the course of 1.5 hours at a reaction temperature of 60° C. The working-up and saponification to give 2-nitro-3-amino-pyridine corresponds to that of Example 1. The yield and quality of the reaction product was also identical with Example 1.

(B) COMPARISON EXAMPLES

Various 3-aminopyridine derivatives, prepared by introducing other protective groups for the amino group, were nitrated analogously to Example (of the invention) 1b. In so doing, the reaction was carried out under the following reaction conditions:

Reaction temperature: approx. 30°–80° C.;
concentration H$_2$SO$_4$ (96% strength);
starting material: H$_2$SO$_4$ molar ratio=1:(5–10);
Amount of HNO$_3$: 120–200%, relative to the starting material.

The reaction products were hydrolyzed as in Example (of the invention) 1C. The results are summarized in the following table:

| | Behavior of the pyridine derivatives when nitrated in sulfuric acid | |
| --- | --- | --- |
| Protective group X | Decomposition | no selective nitration in the 2-position |
| —COCH$_3$ | | + |
| —COC$_6$H$_5$ | | + |
| —COC$_6$H$_5$—NO$_2$(-meta) | | + |
| —COOCH$_3$ | + | |
| —COOC$_6$H$_5$ | | + |
| —CON (n-C$_4$H$_9$)$_2$ | + | |
| —CON (i-C$_4$H$_9$)$_2$ | + | |
| —CONH C$_4$H$_9$ (n) | + | |
| —CONH C$_4$H$_9$ (i) | + | |
| —SO$_2$C$_6$H$_5$ | | + |

-continued

| Protective group X | Behavior of the pyridine derivatives when nitrated in sulfuric acid | |
|---|---|---|
| | Decomposition | no selective nitration in the 2-position |
| 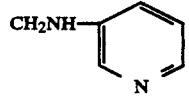 | | + |

As can be seen from the Table, either the protective groups introduced are split off under the conditions of nitration or, if the protective group is stable, there is no selective nitration in the 2-position in the pyridine ring.

We claim:

1. A process for the preparation of 2-nitro-3-aminopyridine which comprises:
   (a) reacting 3-aminopyridine with phosgene ($COCl_2$) or urea ($H_2NCONH_2$) to give N,N'-di-(3-pyridyl)-urea;
   (b) nitrating said N,N'-di-(3-pyridyl)-urea with a mixture of nitric acid and sulfuric acid in a ratio in which the nitric acid is acting as a nitration agent to give N,N'-di-(3-pyridyl)-urea and nitric acid in a molar ratio of 0.5 part of N,N'-di-(3-pyridyl)-urea to about 1 to 2 parts of nitric acid; and
   (c) hydrolyzing said N,N'-di-(2-nitro-3-pyridyl)-urea to give 2-nitro-3-aminopyridine.

2. The process according to claim 1 wherein the nitrating step (b) is carried our at about 50° to 70° C.

3. The process according to claim 1 wherein in the nitrating step (b) the molar ratio of N,N'-di-(3-pyridyl)-urea to nitric acid is about 0.5: about 1.2–1.4.

4. The process according to claim 1 wherein the hydrolysis is carried out in excess water containing a polar solvent.

5. The process according to claim 1 wherein the hydrolysis is carried our in an inorganic base in aqueous $C_1$–$C_4$-alcohol.

6. The process according to claim 1 wherein the reaction temperature does not substantially exceed 90° C.

7. The process according to claim 1 wherein in the nitrating step (b) a mixture of nitric acid and sulfuric acid containing oleum is used.

8. N,N'-di-(2-nitro-3-pyridyl)-urea of the formula

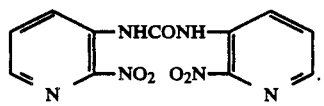

* * * * *